US012778936B2

(12) United States Patent
Bodmeier et al.

(10) Patent No.: US 12,778,936 B2
(45) Date of Patent: Nov. 3, 2026

(54) OPHTHALMIC PREPARATIONS OF MUSCARINIC AGONIST AND METHODS OF USE

(71) Applicant: BIOTHERAVISION, INC., Chicago, IL (US)

(72) Inventors: Roland Bodmeier, Berlin (DE); Chin-Ming Chang, Zhubei City (TW)

(73) Assignee: Biotheravision, Inc., Chicago, IL (US)

(*) Notice: Subject to any disclaimer, the term of this patent is extended or adjusted under 35 U.S.C. 154(b) by 971 days.

(21) Appl. No.: 17/281,587

(22) PCT Filed: Oct. 4, 2019

(86) PCT No.: PCT/US2019/054818
§ 371 (c)(1),
(2) Date: Mar. 31, 2021

(87) PCT Pub. No.: WO2020/072971
PCT Pub. Date: Apr. 9, 2020

(65) Prior Publication Data

US 2021/0369686 A1 Dec. 2, 2021

Related U.S. Application Data

(60) Provisional application No. 62/743,021, filed on Oct. 9, 2018, provisional application No. 62/742,330, filed on Oct. 6, 2018.

(51) Int. Cl.

| | |
|---|---|
| ***A61K 31/439*** | (2006.01) |
| ***A61K 9/00*** | (2006.01) |
| ***A61K 31/436*** | (2006.01) |
| ***A61K 31/4704*** | (2006.01) |
| ***A61K 31/472*** | (2006.01) |
| ***A61K 31/568*** | (2006.01) |
| ***A61K 31/573*** | (2006.01) |
| ***A61K 31/7084*** | (2006.01) |
| ***A61K 38/13*** | (2006.01) |
| ***A61K 47/12*** | (2006.01) |

(52) U.S. Cl.

CPC .......... *A61K 31/439* (2013.01); *A61K 9/0048* (2013.01); *A61K 31/436* (2013.01); *A61K 31/4704* (2013.01); *A61K 31/472* (2013.01); *A61K 31/568* (2013.01); *A61K 31/573* (2013.01); *A61K 31/7084* (2013.01); *A61K 38/13* (2013.01); *A61K 47/12* (2013.01)

(58) Field of Classification Search
None
See application file for complete search history.

(56) References Cited

U.S. PATENT DOCUMENTS

| | | | | |
|---|---|---|---|---|
| 6,410,544 | B1 | 6/2002 | Gwon et al. | |
| 7,491,383 | B2 | 2/2009 | Woodward et al. | |
| 8,957,110 | B2 | 2/2015 | Aleo et al. | |
| 2007/0053964 | A1* | 3/2007 | Isowaki | A61P 27/02 514/397 |
| 2011/0150974 | A1* | 6/2011 | Nakajima | C07D 497/20 514/278 |
| 2012/0003296 | A1 | 1/2012 | Shantha et al. | |
| 2016/0008337 | A1 | 1/2016 | Horn et al. | |

FOREIGN PATENT DOCUMENTS

| | | | |
|---|---|---|---|
| GB | 1459264 | A | 12/1976 |
| JP | 07330604 | A | 12/1995 |
| KR | 20070018755 | A | 2/2007 |
| KR | 20190109677 | A | 9/2019 |

OTHER PUBLICATIONS

Kotreka et al (PLos One 12(2):e0172306, 2017) (Year: 2017).*
Extended European Search Report of European Patent Application 19870003.1, Jun. 22, 2022, 11 pages.
Kaleb, M Pauley, et al., "Altered miR-146a expression in Sjogren's syndrome and its functional role in innate immunity", European Journal of Immunology, vol. 41, No. 7, May 27, 2011, pp. 2029-2039.
Written Opinion of the International Application PCT/US2019/054818, Dec. 11, 2019, 5 pages.
International Preliminary Report on Patentability of the International Application PCT/US2019/054818, Nov. 18, 2020, 15 pages.
Creuzot, C. , et al., "Improvement of dry eye symptoms with polyunsaturated fatty acids", J. Fr. Ophtalmol., vol. 29, No. 8, 2006, pp. 868-873.
Liu, Aihua , et al., "Long-chain and very long-chain polyunsaturated fatty acids in ocular aging and age-related macular degeneration", Journal of Lipid Research, vol. 51, 2010, pp. 3217-3229.
Zhu, Wei , et al., "Efficacy of polyunsaturated fatty acids for dry eye syndrome: a meta-analysis of randomized controlled trials", Nutrition Reviews, vol. 72, No. 10, 2014, pp. 662-671.

* cited by examiner

*Primary Examiner* — Craig D Ricci
(74) *Attorney, Agent, or Firm* — Synergy IP Group AG; Lily Ackerman

(57) ABSTRACT

The present invention provides stable topical ophthalmic preparations of muscarinic agonist for the treatment of dry eye disease. The composition can include a polyunsaturated fatty acid.

17 Claims, No Drawings

OPHTHALMIC PREPARATIONS OF MUSCARINIC AGONIST AND METHODS OF USE

CROSS REFERENCE TO RELATED APPLICATIONS

This application is a United States National Stage Application filed under 35 U.S.C. § 371 claiming the benefit of International Application No. PCT/US2019/054818, filed on Oct. 4, 2019, which claims priority to and the benefit of U.S. Provisional Application No. 62/743,021, filed on Oct. 9, 2018, and U.S. Provisional Application No. 62/742,330, filed on Oct. 6, 2018, all of which are incorporated herein by reference in their entireties.

FIELD OF THE INVENTION

The invention relates to ophthalmic preparations comprising muscarinic agonist alone or in combination with one or more additional active agents such as a steroid, an immunomodulator, a hormone, secretagogue, and/or polyunsaturated fatty acids (PUFA) and methods for using the same for the treatment of dry eye disease.

BACKGROUND OF THE INVENTION

Dry eye disease (DED), also called as keratoconjunctivitis sicca, is a chronic and potentially debilitating condition that involves ocular surface damage, inflammation and symptoms of irritation. It is a multifactorial disorder of the ocular surface that affects an estimated 20 million patients in the United State alone. The Dry Eye Workshop (DEWS) has classified dry eye based upon two basic causal mechanisms: tear deficiency and abnormally rapid tear evaporation. Dry eye disease is also associated with localized inflammation of the ocular surface and periocular tissues. It is unclear as to whether chronic inflammation leads to the clinical manifestations of dry eye disease or, conversely, if dry eye disease leads to chronic inflammation. Due to the complexity of multifactorial causes of dry eye disease and lack of clear understanding of relationship between dry eye disease and inflammation, the attempts in searching for an effective dry eye disease treatment have been vastly unsuccessful and led to collective disappointment for patients and clinicians alike.

Sjogren's syndrome (also known as "Mikulicz disease" and "Sicca syndrome") is labeled as an autoimmune disorder in which immune cells attack and destroy the salivary and lacrimal exocrine glands. It affects 4 million people, second only to rheumatic disease. 90% of patients are woman above the age of 40, although any age group of men and woman can be affected. It can be primary or developing years after rheumatoid arthritis, systemic lupus erythematosus, scleroderma, primary biliary cirrhosis etc. named as Secondary Sjogren's syndrome. There is no cure for Sjogren's syndrome dry eye syndrome, and the treatment is palliative. Artificial tears, goggles to increase local humidity or punctual plugs inserted to help retain tears are of temporary relief.

The pathology of tear deficiencies is a failure to maintain lacrimal gland function in tear secretion. The cause may be due to a failure of the lacrimal glands to produce tears based on a deficiency on the part of the lacrimal glands, an obstruction, systemic drugs that impair the function of the glands, autoimmune disease, or age-related changes in the lacrimal gland. Longtime contact lens wearers and patients who underwent LASIK may also develop deficiencies from the loss of corneal nerve sensation.

Since the majority of tear and tear components come from the lacrimal gland, a decrease in the secretion will result in tear deficiency and further results in corneal epithelium cell damage and inflammation. Moreover, tear secreted from lacrimal gland contains essential enzymes, proteins and antimicrobial components that are crucial to protect and repair corneal epithelium cell damage as a result of dryness of the eye. It is, therefore, rational to target the increase in lacrimal gland secretion as the primary and main treatment of dry eye disease.

Evaporative dry eye is typically caused by Meibomian gland dysfunction and lipid insufficiency that results in increased evaporation and decreased stability in the tear film. Evaporative dry eye causes ocular dry eye symptoms even in the presence of normal tear secretion.

Ocular surface inflammation is among the consequences of tear deficiencies and/or Meibomian gland dysfunction. An immune-based inflammatory response also plays a major part in the corneal epithelial disease and ocular discomfort of dry eye. In light of this, dry eye can be thought of as more than a simple deficiency of one or more tear film components; it is also as an ocular surface inflammatory syndrome. Most patients have a combination of factors that lead to dry eye disease. It is often difficult to point to one particular factor as the cause; instead, dry eye is caused by a cascade of problems or factors that lead to the dry eye disease signs and symptoms.

Typical symptoms of dry eye disease include burning, itching, foreign body sensation, stinging, dryness, photophobia, swelling, ocular fatigue, and/or redness. In some cases, patients may report transient blurring of vision. These symptoms are typically worse later in the day and can be triggered or exacerbated by certain environmental conditions such as low humidity environment.

Several objective tests are commonly used to diagnose dry eye disease signs. Diagnostic dyes are used to identify and monitor changes in the ocular surface, tear break-up time (TBUT) is used to assess the stability and performance of the tears, and the Schirmer test is performed to evaluate tear production. In general, dry eye tests do not correlate well with symptoms, but these tests are mainstays in the field and clinicians continue to find their results useful.

Current treatment of dry eye includes over-the-counter eye drops, a limited number of prescription eye drops, punctum plugs, procedures for treating Meibomian gland disorder, and nutritional supplements. Yet, the effect of these treatments is far from optimal, and there is a great demand for more effective products to be developed for the treatment of dry eye disease. The goals of treatment are to relieve signs and/or symptoms of dry eye, improve the patient's comfort, return the ocular surface and tear film to the normal state, and, whenever possible, prevent corneal damage.

Over the counter eye drops are lubricant eye drops used to treat the dryness and irritation associated with deficient tear production in dry eye disease. Mild disease conditions require the application of lubricant drops four times a day while severe cases need greater frequency (10-12 times a day) of administration.

Restasis, a cyclosporine A topical emulsion, is an immunomodulator which prevents activation of T lymphocytes and hence decreases levels of inflammatory cytokines in the conjunctival epithelium with an increase in goblet cells. Restasis is the first approved topical preparation approved for treatment of dry eye disease.

Diquas, a diquafosol sodium formulation, is a secretagogue that stimulates fluid transport and mucin secretion. The secretagogue also may stimulate lipid production in the meibomian glands. Mucosta, a rebamipide formulation is another secretagogue that is approved in Japan to treat dry eye disease.

Xiidra, Lifitegrast is a recent entry to treat dry eye disease. It inhibits an integrin, lymphocyte function-associated antigen 1 (LFA-1), from binding to intercellular adhesion molecule 1 (ICAM-1). This mechanism is believed to down-regulate inflammation mediated by T lymphocytes.

These are the only approved topical preparations for the treatment of dry eye. Unfortunately, these are not available globally due to suboptimal clinical results.

Other than the aforementioned therapeutic agents for dry eye disease, polyunsaturated fatty acids (PUFA) have been demonstrated to have multiple benefits to the eye when given orally in a large amount. It was reported that long-chain PUFAs play important roles in normal human retinal function and visual development, and some epidemiological studies of PUFA intake suggest a protective role against the incidence of advanced age-related macular degeneration (AMD) (*J Lipid Res.* 2010 November; 51(11): 3217-3229). It was also reported in the literature that high doses of PUFA alleviate dry eye syndromes (*J Fr Ophtalmol.* 2006 October; 29(8):868-73). Its benefit to dry eye was later confirmed through meta-analysis of all relevant randomized controlled trials (*Nutr Rev.* 2014 October; 72(10):662-71. doi: 10.1111/nure.12145. Epub 2014 Sep. 18). Recently, an artificial eye drop compositions based on polyunsaturated Omega-3 and Omega-6 fatty acids was developed by TRB Chemedica International S.A (U.S. Pat. No. 8,957,110) to enable direct administration of PUFAs to the eye.

Two main types of PUFAs are omega-3 and omega-6 fatty acids. Both of these are classified as essential fatty acids, because the human body cannot make them and has to get them from diet. Examples of omega-3 fatty acids include alpha-linolenic acid (ALA), gamma-linolenic acid (GLA), eicosapentaenoic acid (EPA), and docosahexaenoic acid (DHA). Linolenic acid (LA) and arachidonic acid (AA) are examples of omega-6 fatty acids.

Cevimeline (CAS 107233-08-9 or CAS 153504-70-2 (HCl salt hemihydrate); (2R,2R)-2'-Methylspiro[4-azabicyclo[2.2.2]octane-2,5'-[1,3]oxathiolane];cis-2'-Methyl-spiro [1-azabicyclo[2.2.2]octane-3,5'-[1,3]oxathiolane] hydrate hydrochloride) and pilocarpine (CAS 92-13-7, 54-71-7 (HCl salt); (3S,4R)-3-Ethyl-4-((1-methyl-1H-imidazol-5-yl) methyl)dihydrofuran-2(3H)-one) are cholinergic agonists which bind to muscarinic receptors. These muscarinic agonists in sufficient doses can increase secretion of exocrine glands, such as salivary and sweat glands. Both cevimeline and pilocarpine are available in oral preparations and approved by the FDA as systemic muscarinic agonists for the treatment of dry mouth in patients with Sjogren's syndrome. Although these oral dosage products are not approved for treatment of dry eye disease, dry eye is a common problem associated with Sjogren's, and therefore these have been studied to relief dry eye syndromes for patients. Cevimeline oral preparation is approved for the treatment of the dry mouth for Sjogren's syndrome and has also been studied for the treatment of dry eye. But it has not been developed into a stable topical ophthalmic preparation for dry eye disease. While oral cevimeline and pilocarpine have shown significant improvement in treating dry eye disease, they have not been widely accepted due to systemic side effects from oral administration.

Formulations containing cevimeline or pilocarpine have been suggested: US20070053964, US20120003296, and US20160008337. The '964 Publication discloses formulations adapted for percutaneous administration on the outer surface of the eyelid, and said formulations are not suitable for direct administration onto the surface of the eye, because the high content of percutaneous absorption enhancer and high drug concentration would cause significant eye irritation. The '964 Publication included comparative examples of pilocarpine 10% and 20% eye drop solution formulations and a cevimeline 20% eye drop solution formulation administered directly into the eye. The publication suggested that direct administration of pilocarpine or cevimeline solution into the eye is not desirable compare to percutaneous preparations from tear production and side effect perspectives. The '296 Publication discloses ophthalmic formulations requiring insulin or insulin-like growth factor. The '337 Publication discloses ophthalmic formulations requiring a cycloplegic agent.

Pilocarpine is commercially available as topical ocular preparations for treatment of glaucoma, and it has also been reported to relief dry eye disease. However, historically it has been difficult to prepare pilocarpine as a stable and comfortable ophthalmic preparation. Commercial pilocarpine ophthalmic preparations are stinging and irritating when administered to the eye. Pilocarpine topical preparations are also very unstable and high level of undesired degradation impurities are present in commercial pilocarpine ophthalmic products. A key problem has been trying to balance the increased stability at lower pH (around 3-5) and higher irritability against the decreased stability at higher pH (around 7) and lower irritability.

For example, the muscarinic agonist pilocarpine is given topically for the treatment of glaucoma. Pilocarpine topical ophthalmic preparations have to be prepared at an acidic pH range (3.5-5.5) which is irritating to the eye, in order to maintain acceptable stability. Furthermore, muscarinic agonist stimulates contraction of the sphincter muscle and produces miosis. Patients often experience adverse reactions such as burning or discomfort, temporal or periorbital headache, ciliary spasm, conjunctival vascular congestion, superficial keratitis and induced myopia.

Many treatments for dry eye disease have been attempted but failed over the years by various companies. Ophthalmic use of a muscarinic agonist, pilocarpine, prepared at an acidic pH range (3.5-5.5) which is irritating to the eye, has been reported for dry eye diseases. However, ophthalmic use of a muscarinic agonist prepared at a neutral pH range and a drug concentration range suitable for direct administration into the eye for the treatment of dry eye disease have not been reported.

It is clear that there is an unmet medical need to develop pharmaceutically stable, comfortable, safe, minimally irritating or non-irritating and effective muscarinic receptor agonist-based preparations for direct topical administration to the surface of eye for the treatment of dry eye.

SUMMARY OF THE INVENTION

The present invention provides stable topical ophthalmic composition(s) for the treatment of dry eye disease, keratoconjunctivitis. Said composition promotes secretion of lacrimal fluid, thereby treating dry eye disease. In particular, the compositions described herein provide stable compositions comprising a therapeutically effective amount of muscarinic agonist suitable for ophthalmic use.

The present invention is based on the surprising discovery that an effective amount of muscarinic receptor agonist can be provided in a stable and topically acceptable ophthalmic compositions at neutral physiology pH range that can be instilled onto the surface of eye with minimal to no irritation and be utilized to mitigate the signs or symptoms of dry eye disease. Suitable for ophthalmic use means that the composition can be administered topically directly onto any surface of the eye and/or eye socket, e.g. sclera, cornea, conjunctiva, conjunctival sac, among other such surfaces. The composition is not intended for percutaneous administration to the outer surface of the eyelid.

The ophthalmic composition is an aqueous (meaning containing water as the primary component) liquid or viscous liquid composition. In some embodiments, the composition excludes an ointment composition, cream composition, insert composition, punctum composition, plaster composition, paste composition, and/or non-aqueous composition.

The composition is preferably sterile. The composition is preferably about isotonic with tear (lacrimal) fluid, meaning the tonicity (osmolality) of the composition is in the range of about 200 to about 400 milliosmoles/liter (mOsm/L) or preferably from about 240 to about 360 mOsm/L.

The composition preferably exhibits about the same pH as lacrimal fluid, meaning the composition has pH in the range of about 6 to about 9, about 6 to about 8, about 7 to about 9, about 6.5 to about 8.5, or about 7 to about 8.

An aspect of the invention provides a stable ophthalmic composition comprising (or consisting essentially of or consisting of) an effective amount of at least one muscarinic receptor agonist, wherein said composition is therapeutically effective and stable at neutral pH. In some embodiments, the subject is suffering from dry eye disease (disorder), Sjogren syndrome, Meibomian gland dysfunction, ocular inflammation, keratoconjunctivitis, ocular inflammation, and/or ocular irritation.

The invention also provides a method of treating dry eye disease comprising topically administering directly to the eye of a subject in need thereof one or more doses of an ophthalmic composition comprising at least one muscarinic receptor agonist. The present invention is focused on stimulation of lacrimal gland tear product as the primary mode of action for the treatment of dry eye disease.

An exemplary muscarinic receptor agonist is an M3 muscarinic receptor agonist (MRA). The MRA can be selected from the group consisting of aceclidine, acetylcholine, bethanechol, carbachol, cevimeline, oxotremorine, pilocarpine, any M3 muscarinic receptor agonist that has therapeutic effect to treat dry eye disease, and a combination of any two or more thereof.

Another aspect of the invention provides a stable ophthalmic combination formulation comprising (or consisting essentially of or consisting of) an effective amount of at least one muscarinic receptor agonist and one or more other active ingredients. The invention also provides a method of treating dry eye disease comprising topically administering directly to the eye of a subject in need thereof one or more doses of an ophthalmic combination composition comprising at least one muscarinic receptor agonist and one or more other active ingredients.

In some embodiments, exemplary one or more other active ingredient(s) can be selected from the group consisting of a) at least one steroid; b) at least one immunomodulator; c) at least one hormone; d) at least one secretagogue; e) a lymphocyte function associated antigen-1 (LFA-1) antagonist; and f) active ingredient effective for treating Meibomian gland dysfunction. In preferred embodiments, exemplary other active ingredient can be selected from the group consisting of a) at least one steroid such as loteprednol etabonate, prednisolone acetate, fluticasone; b) at least one immunomodulator (immunosuppressant) such as cyclosporine, tacrolimus, sirlolimus; c) at least one hormone such as testosterone, estrogen; d) at least one secretagogue such as rebamipide or diquafosol; and e) a lymphocyte function associated antigen-1 (LFA-1) antagonist.

In some embodiments, the ophthalmic composition excludes insulin, IGF (insulin-like growth factor), somatomedin C, and cycloplegic agent. In some embodiments, the ophthalmic composition excludes an active ingredient not disclosed herein.

In some embodiments, the ophthalmic composition includes cevimeline as the sole active ingredient (drug) even though it will also include one or more pharmaceutically acceptable excipients.

Another aspect of the invention provides a stable ophthalmic composition comprising (or consisting essentially of or consisting of) an effective amount of at least one muscarinic receptor agonist and at least one polyunsaturated fatty acid (PUFA), wherein said composition is therapeutically effective and stable at neutral pH range. In some embodiments, the subject is suffering from dry eye disease (disorder), Sjogren syndrome, Meibomian gland dysfunction, ocular inflammation, and/or ocular irritation.

The PUFA is a fatty acid comprising about 12 to about 26 carbon atoms per molecule. Homologs and derivatives of said PUFA is contemplated within the scope of the invention. Mixtures of two of more PUFA's is contemplated within the scope of the invention. In some embodiments, the PUFA is selected from the group consisting of omega-3 fatty acid and omega-6 fatty acid. Exemplary PUFA's include eicosapentaenoic acid (EPA), docosahexaenoic acid (DHA), alpha-linolenic acid (ALA), gamma-linolenic acid (GLA), or mixture of thereof.

In preparing the ophthalmic composition, the PUFA can be added as a separate ingredient from the MRA. Alternatively, the PUFA is included as part of an ion pair comprising the MRA and the PUFA.

The invention also provides an ophthalmic composition comprising mixture comprising at least one PUFA and at least one MRA. In some embodiments, the invention also provides an ophthalmic composition comprising at least one ion pair complex comprising at least one PUFA and at least one MRA present in a therapeutically effective amount. Said PUFA-containing compositions can be used to treat diseases or disorders of the eye, such as described herein or as may otherwise be found to be therapeutically responsive to MRA.

In some embodiments, the MRA is cevimeline or one or more salts thereof. In some embodiments, the MRA is selected from the group consisting of cevimeline, one or more salts of cevimeline, and a combination thereof. In some embodiments, the MRA is selected from the group consisting of pilocarpine, one or more salts of pilocarpine, and a combination thereof. In some embodiments, the MRA is selected from the group consisting of cevimeline, one or more salts of cevimeline, pilocarpine, one or more salts of pilocarpine, and a combination thereof.

The MRA of the invention can be present as one or more forms in a composition of the invention. The form of the MRA is independently selected upon each occurrence from the free base form and salt form. A composition can comprise the MRA in free base form, in salt form, or in a combination of free base form and salt form. Pharmaceutically acceptable salt forms of the MRA includes those made from PUFA.

In some embodiments, the ophthalmic composition comprises cevimeline (CEV) as the only active ingredient. CEV can be present at a concentration of 0.1% to 10.0% (w/v).

In another particular embodiment, the invention provides a stable ophthalmic composition of MRA in combination with loteprednol etabonate (steroid) and one or more pharmaceutically acceptable excipients. In certain embodiments, cevimeline is present in the composition at a concentration of 0.1% to 10.0% (w/v), or any value within said range. In certain embodiments, loteprednol etabonate (steroid) is present in the composition at a concentration of 0.1% to 1.0% w/v or any value within said range, or about 0.5% w/v.

In another particular embodiment, the invention provides a stable ophthalmic composition of MRA in combination with cyclosporine (immunosuppressant, immunomodulator) and one or more pharmaceutically acceptable excipient. In certain embodiments, cevimeline is present in the composition at a concentration of 0.1% to 10.0% (w/v), or any value within said range. In certain embodiments, cyclosporine (immunosuppressant) is present in the composition at a concentration of 0.05% to 0.1% (w/v), or any value within said range.

In another particular embodiment, the invention provides a stable ophthalmic composition of MRA in combination with hormone (androgen, e.g. testosterone) and one or more pharmaceutically acceptable excipient. In certain embodiments, cevimeline is present in the composition at a concentration of 0.1% to 10.0% (w/v), or any value within said range. In certain embodiments, hormone is present in the composition at a concentration of 0.01% to 0.5% w/v, 0.03% to 0.5% w/v, 0.05% to 0.5% w/v.

In another particular embodiment, the invention provides a stable ophthalmic composition of MRA in combination with secretagogue (e.g. diquafosol or its salts) and one or more pharmaceutically acceptable excipient. In certain embodiments, cevimeline is present in the composition at a concentration of about 0.1% to about 10.0% (w/v), or any value within said range. In certain embodiments, diquafosol is present in the composition at a concentration of about 1.0% to about 5.0% (w/v), or any value within said range. In certain embodiments, lifitegrast is present in the composition at a concentration of about 1.0% to about 5.0% or about 1.0% to about 10.0% (w/v), or any value within said range.

In some embodiments, the composition comprises the specified active ingredient(s) and a vehicle comprising one or more pharmaceutically acceptable excipients, such as at least one tonicity-adjusting agent (tonicity modifier), at least one buffering agent, at least one stabilizing agent, at least one surfactant, at least one solubilizer, at least one viscosity-modifying (enhancing) agent, at least one antioxidant, at least one acid, at least one base, at least one chelating agent, at least one preservative or a combination of any two or more thereof.

The invention includes all combinations of the aspects, embodiments and sub-embodiments disclosed herein. Other features, advantages and embodiments of the invention will become apparent to those skilled in the art by the following description, accompanying examples and appended claims.

DETAILED DESCRIPTION OF THE INVENTION

The ophthalmic composition comprises at least one MRA and one or more pharmaceutically acceptable excipients in an aqueous vehicle, meaning a primarily water-containing vehicle. The aqueous vehicle can be present as purified water, lacrimal fluid and/or autologous serum.

The invention is based in part on the discovery that cevimeline can be prepared as a stable and comfortable neutral pH composition for ocular use particularly for dry eye disease treatment. Said formulation has a neutral pH and suitable to the eye following topical administration. The MRA, e.g. cevimeline, containing composition exhibits high storage stability at room temperature, i.e. from 15-25° C. In some embodiments, the MRA undergoes less than 3% w of degradation during 18-24 months storage period at 25° C.

The invention features novel topical ophthalmic composition(s) comprising an effective amount of cevimeline, as free base and/or a pharmaceutically acceptable salt thereof, in a pharmaceutically acceptable preparation. In particular embodiments, the invention provides stable ophthalmic preparations of cevimeline as the only active agent in the preparations. The invention also features ophthalmic preparations of cevimeline in combination with one or more additional active ingredients selected from cyclosporine, loteprednol etabonate, testosterone, diquafosol or its salts, and/or lifitegrast.

In preparing the ophthalmic composition, the PUFA can be added as a separate ingredient from the MRA. In some embodiments, the PUFA is present at a concentration of about 0.1%-10.0% w/v, or more preferably 0.2%-5.0% w/v, or more preferably 0.5%-2.0% w/v. Alternatively, the PUFA is included as part to form ion pair between MRA and the PUFA. The molar ratio of PUFA to MRA is in the range of about 2:1 to about 1:2, or about 1:1.

The present invention also provides a pharmaceutically stable topical ophthalmic preparation comprising polyunsaturated fatty acid (PUFA) ion paired with muscarinic agonist amine drug for the treatment of ocular pathologies, in particular for dry eye disease.

The PUFA can be selected from the group consisting of essential fatty acids containing more than one double bond in their backbone. Exemplary suitable PUFA's include omega-3 fatty acids and omega-6 fatty acid. Exemplary omega-3 fatty acids include alpha-linolenic acid (ALA), eicosapentaenoic acid (EPA), docosahexaenoic acid (DHA) and other known homologs and derivatives of such acids. Exemplary omega-6 fatty acids include linoleic acid (LA), gamma-linolenic acid (GLA), and other known homologs and derivatives of such acids.

In some embodiments, the invention provides ophthalmic preparations comprising an effective amount of cevimeline and cyclosporine. Such preferred combination preparations are effective in further mitigating the signs and symptoms of dry eye disease.

In another embodiment, the invention provides an ophthalmic preparation comprising an effective amount of cevimeline and testosterone.

In another embodiment, the invention provides an ophthalmic preparation comprising an effective amount of cevimeline and diquafosol.

In another embodiment, the invention provides an ophthalmic preparation comprising an effective amount of cevimeline and lifitegrast.

In another embodiment, the invention provides a stable ophthalmic preparation of PUFA ion paired with cevimeline. In certain embodiments, cevimeline is present in the preparation at a concentration of about 0.1% to about 10.0% (w/v), or any value within said range.

The stability, comfort, safety, and efficacy of the ophthalmic preparations of the invention could not have been predicted by one skilled in the art.

Pharmaceutical compositions comprising an effective amount of cevimeline along or in combination of loteprednol etabonate, cyclosporine, testosterone, diquafosol or its salts which are formulated for ophthalmic administration are disclosed herein. The preparations are for treating dry eye disease.

A preparation for ophthalmic administration is formulated such that it can be administered topically to the eye. The comfort should be maximized as much as possible, although sometimes preparation considerations (e.g. drug stability) may necessitate less than optimal comfort.

Unless indicated otherwise, all ingredient concentrations are presented in units of weight/volume (% w/v).

In certain compositions, the concentration of cevimeline is in the range of about 0.1% to about 10.0%.

In certain compositions, the concentration of cevimeline is from 0.1% to 10.0% and loteprednol etabonate is from 0.1% to 0.5%.

In certain compositions the concentration of cevimeline is in the range of about 0.1% to about 10.0% and the concentration of cyclosporine is in the range of about 0.05% to about 0.1%, about 0.01% to about 0.1%, or about 0.03% to about 0.1%.

In certain compositions, the concentration of cevimeline is in the range of about 0.1% to about 10.0% and concentration of testosterone is in the range of about 0.01% to about 0.1%.

In certain compositions, the concentration of cevimeline is in the range of about 0.1% to about 10.0% and the concentration of diquafosol is in the range of about 1% to about 3.0%. or about 1% to about 5% w/v In certain embodiment, the ophthalmic composition of present invention has a pH from about 6 to about 9 or preferably from about 7 to about 8. The pH of lacrimal fluid is about 7.4. It is understood that acid or base can be used to adjust the pH of the composition as needed.

The ophthalmic composition may or may not be isotonic. In some embodiments, the ophthalmic composition of present invention has an osmolality from about 200 to about 400 milliosmoles/liter (mOsm/L) or preferably from about 240 to about 360 mOsm/L. In some embodiments, the composition comprises about 0.9% NaCl, or about 0.7% to about 1.5% NaCl.

A pharmaceutical composition (formulation) according to the present invention may include one or more pharmaceutically acceptable excipients selected from the group consisting of buffering agent(s), tonicity-adjusting agent(s), surfactant(s), solubilizer(s), viscosity-modifying (enhancing) agent(s), pH-adjusting agent(s) (e.g. acid and/or base), chelating agent(s), preservative(s), antioxidant(s), or a combination of any two or more thereof.

Exemplary buffering agents include, but are not limited to, phosphate salt, borate salt, citrate salt, acetate salt, carbonate salt, bicarbonate salt, borate-polyol complexes, boric acid, sodium acetate, amino acid, Tris, bicarbonate, BIS-Tris, or salt thereof, combinations thereof and the like. The buffering agent(s) can be present in an amount ranging from about 5-200 mM, or about 10-100 mM.

Examples of tonicity-adjusting agents include, but are not limited to mannitol, sorbitol, potassium chloride, sodium chloride, xylitol, glycerin, trehalose, taurine, erythritol, combinations thereof, and the like. The amount of tonicity-adjusting agent in the composition will be that amount required to render the composition isotonic, e.g. isotonic with lacrimal fluid.

Examples of surfactants include, but are not limited to poloxamers, tyloxapol, polysorbate such as polysorbate 80, polysorbate 20, polyoxyethylene castor oil derivatives, sorbitan esters, combinations thereof and the like. The composition typically comprises less than 5%, less than 2% or less than 1% of surfactant. Some embodiments of the invention exclude surfactant.

Examples of solubilizers include, but are not limited to solutol, soluplus, cyclodextrin(s), vegetable oils, combinations thereof, and the like. The composition typically comprises less than 5%, less than 2% or less than 1% of solubilizer(s). Some embodiments of the invention exclude solubilizer(s).

Viscosity-modifying (enhancing) agents are hydrophilic polymers that are added to ocular solutions for two main reasons: (1) to control the rate at which the drop flows out of the container (and thus enhance ease of application); and, more importantly, (2) to control the residence time of the solution within the precorneal environment. The viscosity of the ophthalmic composition is less than about 55 mPa/s or less than about 30 mPa/s.

Examples of viscosity-modifying (enhancing) agents include, but are not limited to carboxymethylcellulose, hyaluronic acid, chondroitin sulfate, polyvinyl alcohol, hydroxypropyl methylcellulose, polylysine, polyacrylic acid, polyacrylamides, N-(2-Hydroxypropyl) methacrylamide (HPMA), xanthan gum, pectins, chitosan, dextran, hydropropylcellulose, hydroethyl cellulose, carrageenan, guar gum, polyoxyl stearate 40, polyvinylpyrrolidone, polyethylene glycol, propylene glycol, combinations thereof and the like.

Hydroxypropylmethylcellulose (Hypromellose USP). Hydroxypropylmethylcellulose (HPMC) is a partially methylated and O-(2-hydroxypropylated) cellulose derivative. In aqueous ocular formulations HPMC is used in the concentration of 0.45-1.0% w/w (the actual concentration being dependent on the molecular weight of polymer used).

Poly(vinyl alcohol). This is a water-soluble vinyl polymer that is available in three grades: (1) high-viscosity (average molecular weight 200 000 g/mol); (2) medium-viscosity (average molecular weight 130 000 g/mol); and (3) low-viscosity (average molecular weight 20 000 g/mol). It is used to enhance the viscosity of ocular formulations in concentrations ranging from 0.25% to 3.00% w/w (the actual concentration being dependent on the molecular weight of polymer used).

Poly(acrylic acid). This is a water-soluble acrylate polymer that is cross-linked with either allyl sucrose or allyl ethers of pentaerythritol. It is predominantly used in ocular aqueous formulations for the treatment of dry-eye syndrome. However, it may be used to increase the viscosity of ocular formulations that contain a therapeutic agent.

Exemplary preservatives include, but are not limited to benzalkonium chloride, benzethonium chloride, p-oxybenzoates such as methyl p-oxybenzoate or ethyl p-oxybenzoate, benzyl alcohol, phenethyl alcohol, sorbic acid or salt thereof, citric acid or salt thereof, thimerosal, chlorobutanol, quaternary amine, chlorhexidine gluconate, stabilized oxychloro complex, combinations thereof, and the like. The preservative, if included, will be present in an amount required to pass USP and/or Ph. Eur. antimicrobial preservative effective test required for eye drops.

Benzalkonium chlorides can be used in ocular solutions/suspensions at a concentration between 0.002% and 0.02% w/v (typically 0.005-0.01% w/v). It is customary to include 0.01-0.1% w/v disodium edetate (disodium EDTA) in ocular formulations in which benzalkonium chloride is used. Benzethonium chloride (unlike benzalkonium chloride) is a pure compound (and not a mixture of compounds). It is commonly used in ophthalmic formulations within the concentration range 0.01-0.02% w/v (although it has been reported to exhibit lower antimicrobial activity than benzalkonium chloride. Esters of parahydroxybenzoates (parabens) can be used. Mixtures of methyl and propyl esters of parahydroxybenzoic acid are used in ophthalmic formulations typically at a combined concentration of 0.2% w/w. Non-irritating (meaning not eye-irritating) organic alcohols can be used as preservatives for ophthalmic formulations: (1) chlorobutanol; and (2) phenylethylalcohol. Chlorobutanol is used in ocular formulations at a concentration of circa 0.5% w/v. Phenylethylalcohol has similar properties to chlorobutanol. The typical concentration used in ophthalmic preparations is 0.25-0.50% v/v. Typical concentration of preservative is within an effective amount required to pass USP and/or Ph. Eur. antimicrobial preservative effective test for eye drops.

Antioxidant may be added to the ophthalmic composition. As used herein, the term "antioxidant" is intended to mean an agent that inhibits oxidation and thus is used to prevent the deterioration of preparations by the oxidative process. Exemplary antioxidants include, but are not limited to, ascorbic acid, malic acid, citric acid, sodium citrate, butylated hydroxyanisole, butylated hydroxytoluene (BHT), propyl gallate, sodium ascorbate, sodium metabisulfite, sodium bisulfite, amino acids, ascorbyl palmitate, hypophophorous acid, monothioglycerol, propyl gallate, sodium formaldehyde sulfoxylate, and other materials known to one of ordinary skill in the art and mixtures thereof. If present, the amount (concentration) of antioxidant will be sufficient to minimize oxidative degradation of one or more active ingredients.

Examples of the alkaline agents that may be used as pH adjusting agents, include, but are not limited to sodium hydroxide (NaOH), potassium hydroxide (KOH), tromethamine, monoethanolamine, sodium bicarbonate ($NaHCO_3$) and other organic and inorganic bases.

Examples of the acidic agents that may be used as pH adjusting agents include but are not limited to hydrochloric acid (HCl), citric acid, tartaric acid, lactic acid, acetic acid, and other organic and inorganic acids and the like and mixtures thereof.

Examples of chelating agents include, but are not limited to sodium edetate (EDTA, ethylenediaminetetraacetic acid salt), sodium citrate, condensed sodium phosphate, combinations thereof and the like. The amount of chelating agent(s) typically ranges from about 0.01-0.2% w/v.

Unless specified otherwise, the term cevimeline is taken to mean the free base form, salt form, or mixture of free base form. and salt form. Unless specified otherwise, the term pilocarpine is taken to mean the free base form, salt form, or mixture of free base form. and salt form. Unless specified otherwise, the term MRA is taken to mean the free base form, salt form, or mixture of free base form. and salt form.

The following embodiments are specifically contemplated:

Embodiment 1. A stable aqueous topical ophthalmic composition comprising about 0.1% to 10% of cevimeline at a neutral pH range of pH 6-9, and one or more pharmaceutically acceptable excipients.

Embodiment 2. The composition of 1, wherein cevimeline is present as the free base form, salt form, or a combination of free base and salt form.

Embodiment 3. The composition of embodiment 1 or 2, wherein the cevimeline is present at a concentration of about 0.1% to about 10% w/v, about 0.5% to about 5% w/v, or about 0.2% to about 2% w/v.

Embodiment 4. The composition of any one of the above embodiments further comprising at least one PUFA.

Embodiment 5. The composition of embodiment 4, wherein the PUFA is present at a concentration of about 0.1%-to about 10% w/v, about 0.5% to about 5% w/v, or about 0.2% to about 2% w/v.

Embodiment 6. The composition of embodiment 4 or 5, wherein said PUFA comprises about 12 to about 26 carbon atoms per molecule.

Embodiment 7. The composition of embodiment 4, 5, or 6, wherein said PUFA is selected from the group consisting of omega-3 fatty acid, omega-6 fatty acid, and a mixture thereof.

Embodiment 8. The composition of embodiment 4, 5, 6, or 7, wherein said PUFA is selected from the group consisting of eicosapentaenoic acid (EPA), docosahexaenoic acid (DHA), alpha-linolenic acid (ALA), gamma-linolenic acid (GLA), and a mixture thereof.

Embodiment 9. The composition of any one of the above embodiments further comprising buffering agent, tonicity modifier, and water.

Embodiment 10. The composition of embodiment 9 optionally further comprising one or more of at least one preservative(s), at least one chelating agent(s), at least one viscosity-modifying agent(s), at least one surfactant(s), at least one solubilizer(s), and/or at least one antioxidant(s).

Embodiment 11. The composition of any one of the above embodiments, wherein said composition has an osmolality in the range of about 200 to about 400 mOsm/L and a pH in the range of about 6 to about 9.

Embodiment 12. The composition of any one of the above embodiments further comprising one or more other active ingredient(s) selected from the group consisting of a) at least one steroid; b) at least one immunomodulator (immunosuppressant); c) at least one hormone (androgen); d) a lymphocyte function associated antigen-1 (LFA-1) antagonist; and f) at least one active ingredient effective for treating Meibomian gland dysfunction.

Embodiment 13. The composition of embodiment 12, wherein a) said steroid is present at a concentration in the range of about 0.1% to about 1% w/v; b) said immunomodulator is present at a concentration in the range of about 0.05% to about 0.1% w/v; c) said hormone is present at a concentration in the range of about 0.01% to about 0.5% w/v; or d) said secretagogue is present at a concentration in the range of about 1% to about 5% w/v; or e) said lymphocyte function associated antigen-1 (LFA-1) antagonist in the range of about 1% to about 5% w/v.

Embodiment 14. The composition of embodiment 12 or 13, wherein a) said steroid is loteprednol etabonate, prednisolone acetate, fluticasone, or a combination thereof; b) said immunomodulator is cyclosporine, tacrolimus, sirlolimus, or a combination thereof; c) said hormone is testosterone, estrogen, or a combination thereof; d) said secretagogue is rebamipide, diquafosol, or a combination thereof; or e) said lymphocyte function associated antigen-1 (LFA-1) antagonist is lifitegrast.

Embodiment 15. The composition of any one of the above embodiments, wherein said composition excludes an ointment composition, cream composition, plaster composition, paste composition, and non-aqueous composition.

Embodiment 16. The composition of any one of the above embodiments, wherein said composition excludes insulin, IGF (insulin-like growth factor), somatomedin C, and cycloplegic agent.

Embodiment 17. The composition of any one of the above embodiments, wherein cevimeline is replaced with pilocarpine, aceclidine, acetylcholine, bethanechol, carbachol, oxotremorine, or any muscarinic receptor agonist that has therapeutic effect to treat dry eye disease.

Embodiment 18. An ophthalmically acceptable ion-pair comprising a muscarinic receptor agonist amine drug and a fatty acid component selected from the group consisting of polyunsaturated fatty acids (PUFA) for the treatment of dry eye disease.

Embodiment 19. The ion-pair of embodiment 18, wherein the molar ratio of PUFA to muscarinic receptor agonist amine drug is in the range of about 2:1 to 1:2, or about 1:1.

Embodiment 20. The ion-pair of embodiment 18 or 19, wherein a) said PUFA comprises about 12 to about 26 carbon atoms per molecule or a mixture thereof; b) said PUFA is selected from the group consisting of omega-3 fatty acid, omega-6 fatty acid, or a combination thereof; or c) said PUFA is selected from the group consisting of eicosapentaenoic acid (EPA), docosahexaenoic acid (DHA), alpha-linolenic acid (ALA), gamma-linolenic acid (GLA), or a mixture thereof.

Embodiment 21. The composition of any one of embodiments 1-17 further comprising the ion-pair of any one of embodiments 18-20.

Embodiment 22. A method of treating a dry eye disorder, disease or condition comprising topically administering to the eye of a subject in need thereof, a composition according to any one of embodiments 1-17.

Embodiment 23. A method of treating a dry eye disorder, disease or condition comprising topically administering to the eye of a subject in need thereof, an ion-pair according to any one of embodiments 18-20.

Exemplary Composition 1A: comprising cevimeline (about 0.1% to about 10.0% w/v), buffering agent, tonicity modifier, and water; osmolality in the range of about 200 to about 400 mOsm/L, pH in the range of about 6 to about 9; optionally further comprising preservative(s), chelating agent(s), viscosity-modifying agent(s), surfactant(s), solubilizer(s), and/or antioxidant(s).

Exemplary Composition 1B: comprising cevimeline (about 0.1% to about 10.0% w/v), steroid (about 0.1% to about 1% w/v), buffering agent, tonicity modifier, and water; osmolality in the range of about 200 to about 400 mOsm/L, pH in the range of about 6 to about 9; optionally further comprising preservative(s), chelating agent(s), viscosity-modifying agent(s), surfactant(s), solubilizer(s), and/or antioxidant(s).

Exemplary Composition 1C: comprising cevimeline (about 0.1% to about 10.0% w/v), immunosuppressant (about 0.05% to about 0.1% w/v, or about 0.1 to about 1 mg/mL, or about 0.5 mg/mL), buffering agent, tonicity modifier, and water; osmolality in the range of about 200 to about 400 mOsm/L, pH in the range of about 6 to about 9; optionally further comprising preservative(s), chelating agent(s), viscosity-modifying agent(s), surfactant(s), solubilizer(s), and/or antioxidant(s).

Exemplary Composition 1D: comprising cevimeline (about 0.1% to about 10.0% w/v), androgen (about 0.01% to about 0.5% w/v), buffering agent, tonicity modifier, and water; osmolality in the range of about 200 to about 400 mOsm/L, pH in the range of about 6 to about 9; optionally further comprising preservative(s), chelating agent(s), viscosity-modifying agent(s), surfactant(s), solubilizer(s), and/or antioxidant(s).

Exemplary Composition 1E: comprising cevimeline (about 0.1% to about 10.0% w/v), secretagogue (about 1% to about 5% w/v), buffering agent, tonicity modifier, and water; osmolality in the range of about 200 to about 400 mOsm/L, pH in the range of about 6 to about 9; optionally further comprising preservative(s), chelating agent(s), viscosity-modifying agent(s), surfactant(s), solubilizer(s), and/or antioxidant(s).

Exemplary Composition 1F: comprising cevimeline (about 0.1% to about 10.0% w/v), AARA (about 0.01% to about 0.1% w/v, about 0.025% w/v), buffering agent, tonicity modifier, and water; osmolality in the range of about 200 to about 400 mOsm/L, pH in the range of about 6 to about 9; optionally further comprising preservative(s), chelating agent(s), viscosity-modifying agent(s), surfactant(s), solubilizer(s), and/or antioxidant(s).

Exemplary Composition 1G: comprising cevimeline (about 0.1% to about 10.0% w/v), PUFA (about 0.1% to about 10.0%), buffering agent, tonicity modifier, and water; osmolality in the range of about 200 to about 400 mOsm/L, pH in the range of about 6 to about 9; optionally further comprising preservative(s), chelating agent(s), viscosity-modifying agent(s), surfactant(s), solubilizer(s), and/or antioxidant(s).

Exemplary Composition 1H: comprising cevimeline (about 0.1% to about 10.0% w/v), steroid (about 0.1% to about 1% w/v), PUFA (about 0.1% to about 10.0%), buffering agent, tonicity modifier, and water; osmolality in the range of about 200 to about 400 mOsm/L, pH in the range of about 6 to about 9; optionally further comprising preservative(s), chelating agent(s), viscosity-modifying agent(s), surfactant(s), solubilizer(s), and/or antioxidant(s).

Exemplary Composition 1J: cevimeline (about 0.1% to about 10.0% w/v), immunosuppressant (about 0.05% to about 0.1% w/v, or about 0.1 to about 1 mg/mL, or about 0.5 mg/mL), PUFA (about 0.1% to about 10.0%), buffering agent, tonicity modifier, and water; osmolality in the range of about 200 to about 400 mOsm/L, pH in the range of about 6 to about 9; optionally further comprising preservative(s), chelating agent(s), viscosity-modifying agent(s), surfactant(s), solubilizer(s), and/or antioxidant(s).

Exemplary Composition 1K: comprising cevimeline (about 0.1% to about 10.0% w/v), androgen (about 0.01% to about 0.5% w/v), PUFA (about 0.1% to about 10.0%), buffering agent, tonicity modifier, and water; osmolality in the range of about 200 to about 400 mOsm/L, pH in the range of about 6 to about 9; optionally further comprising preservative(s), chelating agent(s), viscosity-modifying agent(s), surfactant(s), solubilizer(s), and/or antioxidant(s).

Exemplary Composition 1 L: comprising cevimeline (about 0.1% to about 10.0% w/v), secretagogue (about 1% to about 5% w/v), PUFA (about 0.1% to about 10.0%), buffering agent, tonicity modifier, and water; osmolality in the range of about 200 to about 400 mOsm/L, pH in the range of about 6 to about 9;

optionally further comprising preservative(s), chelating agent(s), viscosity-modifying agent(s), surfactant(s), solubilizer(s), and/or antioxidant(s).

Exemplary Composition 1M: comprising cevimeline (about 0.1% to about 10.0% w/v), AARA (about 0.01% to about 0.1% w/v, about 0.025% w/v), PUFA (about 0.1% to about 10.0%), buffering agent, tonicity modifier, and water; osmolality in the range of about 200 to about 400 mOsm/L, pH in the range of about 6 to about 9; optionally further comprising preservative(s), chelating agent(s), viscosity-modifying agent(s), surfactant(s), solubilizer(s), and/or antioxidant(s).

Exemplary Composition 1N: comprising cevimeline (about 0.1% to about 10.0% w/v), lifitegrast (about 1% to 10% w/v, or about 5% w/v), buffering agent, tonicity modifier, and water; osmolality in the range of about 200 to about 400 mOsm/L, pH in the range of about 6 to about 9; optionally further comprising preservative(s), chelating agent(s), viscosity-modifying agent(s), surfactant(s), solubilizer(s), and/or antioxidant(s).

It should be understood, that compounds used in the art of pharmaceutical formulations generally serve a variety of functions or purposes as an excipient. Thus, if a compound named herein is mentioned only once or is used to define more than one term herein, its purpose or function should not be construed as being limited solely to that named purpose(s) or function(s). For example, citric acid may serve as an antioxidant, chelating agent, buffering agent, preservative or antimicrobial agent.

As used herein, a "salt" of an active ingredient refers to a pharmaceutically acceptable salt. As used herein, a "pharmaceutically acceptable salt" refer to a combination of the active ingredient and an acid. Examples of pharmaceutically acceptable salts include, but are not limited to, mineral or organic acid salts of the active ingredient, e.g. the MRA. The pharmaceutically acceptable salts include the conventional non-toxic salts formed, for example, from non-toxic inorganic or organic acids. For example, such conventional non-toxic salts include those derived from inorganic acids such as hydrochloric, hydrobromic, sulfuric, sulfonic, sulfamic, phosphoric, nitric and others known to those of ordinary skill; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill. Lists of suitable salts are found in Remington's Pharmaceutical Sciences, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The amount of therapeutic compound incorporated in each composition (or dosage form(s) containing said composition) will be at least one or more doses and can be selected according to known principles of pharmacy. An effective amount of therapeutic compound is specifically contemplated. By the term "effective amount", it is understood that, with respect to, for example, pharmaceuticals, a pharmaceutically effective amount is contemplated. A pharmaceutically effective amount is the amount or quantity of active ingredient (drug) which is sufficient to elicit the required or desired therapeutic response, or in other words, the amount which is sufficient to elicit an appreciable biological response when administered to a patient.

The following examples are provided to further elucidate the advantages and features of the present invention but are not intended to limit the scope of the invention. The examples are for the illustrative purposes only. Pharmaceutical grade ingredients were used in preparing the formulations described below. The quantitative composition of these examples is presented in the table below.

Formulations comprising cevimeline can be prepared as described in Examples 1 to 4. The following table details the composition of exemplary formulations Cevi-1 through Cevi-8.

TABLE 1

Composition of exemplary cevimeline-containing aqueous liquid formulations

| Ingredient (% w/w) | Cevi-1 | Cevi-2 | Cevi-3 | Cevi-4 | Cevi-5 | Cevi-6 | Cevi-7 | Cevi-8 |
|---|---|---|---|---|---|---|---|---|
| Cevimeline HCl × 0.5 $H_2O$ (free base equivalent) | 0.6 | 0.6 | 0.6 | 0.6 | 0.6 | 0.6 | 0.2 | 2 |
| Citric Acid, monohydrate | 0.014 | 0.014 | 0.014 | 0.014 | 0.014 | 0.014 | 0.014 | 0.014 |
| Sodium phosphate dibasic heptahydrate | 0.268 | 0.268 | 0.268 | 0.268 | 0.268 | 0.268 | 0.268 | 0.268 |
| pH | 7.4 | 7.4 | 7.4 | 7.4 | 7.4 | 7.4 | 7.4 | 7.4 |
| EDTA | 0.01 | 0.00 | 0.01 | 0.00 | 0.01 | 0.00 | 0.00 | 0.00 |
| NaCl | q.s. | q.s. | 0 | 0 | 0 | 0 | q.s. | q.s. |
| sorbitol | 0 | 0 | q.s. | q.s. | 0 | 0 | 0 | 0 |
| Trehalose | 0 | 0 | 0 | 0 | q.s. | q.s.. | 0 | 0 |
| BAK | 0.005 | 0.005 | 0.005 | 0.005 | 0.005 | 0.005 | 0.005 | 0.005 |
| Purified Water | q.s. | q.s. | q.s. | q.s. | q.s. | q.s. | q.s. | q.s. |

In some embodiments, a formulation of the invention comprises about 0.1 to about 10% w/w of at least MRA free base equivalent (active ingredient), about 10-100 mM of citric acid and/or at least one buffering agent, about 0.01-0.2% w/w of at least one chelating agent ([EDTA]), at least one tonicity modifier (osmotic agent) to adjust to isotonicity range of about 200-400 mOsm, and water (remaining amount to achieve 100% weight balance). Optionally, a preservative present in an amount sufficient to pass the requirements of antimicrobial effective test per USP and/or Ph. Eur. requirement for eye drops may be added.

The formulations of the invention can be evaluated according to the Schirmer test, tear Break-up Time (TBUT), lissamine green staining (Van Bijsterveld score), corneal fluorescein staining (Oxford scale) and oculopalpebral examination. Suitable tests are also described in the scientific literature.

The following examples are merely illustrative of some specific embodiments of the invention and should not be construed to define the entire scope of the invention contemplated herein.

Example 1

Cevimeline compositions Cev-1 and Cevi-2 were prepared as follows. Cevimeline HCl salt was added and dissolved in an aqueous solution containing citric acid and sodium phosphate as buffering agents, sodium chloride as a tonicity agent, benzalkonium chloride as a preservative. Edetate disodium (EDTA) was added at a concentration of 0 or 0.01%. Hydrochloric acid and/or sodium hydroxide was added to adjust the pH to ~7.4 if necessary. The composition is further sterile filtered through a 0.22 micron filter. The composition prepared as described above was tested for physical appearance, assay, impurity, pH, and osmolality and was also tested for stability at 25° C., 40° C. after 6 months of storage and 60° C. after 3 months of storage. No significant loss of assay and change of test parameters were observed. The formulation was considered as stable when stored at room temperature.

Example 2

Cevimeline compositions Cev-3 and Cevi-4 were prepared as follows. Cevimeline HCl salt was added and dissolved in an aqueous solution containing citric acid and sodium phosphate as buffering agents, sorbitol as a tonicity agent, benzalkonium chloride as a preservative. Edetate disodium (EDTA) was added at a concentration of 0 to 0.01%. Hydrochloric acid and/or sodium hydroxide was added to adjust the pH to ~7.4 if necessary. The composition is further sterile filtered through a 0.22 micron filter. The composition prepared as described above was tested for physical appearance, assay, impurity, pH, and osmolality. The composition prepared as described above was tested for physical appearance, assay, impurity, pH, and osmolality and was also tested for stability at 25° C. up to 27 months 40° C. after 6 months and 60° C. after 6 months of storage. No significant loss of assay and change of test parameters were observed. The formulation was considered as stable when stored at room temperature.

Example 3

Cevimeline compositions Cev-5 and Cevi-6 were prepared as follows. Cevimeline HCl salt was added and dissolved in an aqueous solution containing citric acid and sodium phosphate as buffering agents, trehalose as a tonicity agent, benzalkonium chloride as a preservative. Edetate disodium (EDTA) was added at a concentration of 0 to 0.01%. Hydrochloric acid and/or sodium hydroxide was added to adjust the pH to ~7.4 if necessary. The composition is further sterile filtered through a 0.22 micron filter. The composition prepared as described above was tested for physical appearance, assay, impurity, pH, and osmolality and was also tested for stability at 25° C. up to 27 months, 40° C. after 6 months and 60° C. after 6 months of storage. No significant loss of assay and change of test parameters were observed. The formulation was considered as stable when stored at room temperature.

Example 4

Cevimeline compositions Cev-7 and Cevi-8 were prepared as follows. Cevimeline HCl salt was added and dissolved in an aqueous solution at a concentration of 0.2% and 2.0% containing citric acid and sodium phosphate as buffering agents, sodium chloride as a tonicity agent, benzalkonium chloride as a preservative. Edetate disodium (EDTA) was added at a concentration of 0 to 0.01%. Hydrochloric acid and/or sodium hydroxide was added to adjust the pH to ~7.4 if necessary. The composition is further sterile filtered through a 0.22 micron filter. The composition prepared as described above was tested for physical appearance, assay, impurity, pH, and osmolality and was also tested for stability at 25° C. up to 27 months, 40° C. after 6 months and 60° C. after 6 months of storage. No significant loss of assay and change of test parameters were observed. The formulation was considered as stable when stored at room temperature.

Example 5

Formulations comprising cevimeline, prepared essentially as described in Examples 1 to 4 herein, were subjected to real time (25° C.) and accelerated (40° C. and 60° C.) stability conditions. HPLC assay was performed to evaluate cevimeline and impurity (degradant) content along with other quality attributes (pH, osmolality and physical appearance). All formulations were found to be stable.

TABLE 2A

Stability of Example Cevimeline Formulations

| | | Time | Storage condition 25° C./60% RH Time, months | | | |
|---|---|---|---|---|---|---|
| Formulation | Parameter | 0 | 3 | 6 | 10 | 27 |
| Cevi-1 | Assay, % | 100.8 | 99.9 | 97.4 | 99.3 | 99.4 |
| | RS, % | 0.15 | 0.17 | 0.17 | 0.20 | 0.05 |
| | pH | 7.3 | 7.3 | 7.4 | 7.2 | 7.1 |
| | Osmolality, mOsmol/kg | 287 | 286 | 291 | 312 | 296 |
| | Physical appearance | Colourless, clear solution (CC) | CC | CC | CC | CC |
| Cevi-2 | Assay, % | 100.6 | 99.9 | 100.5 | 99.8 | 100.2 |
| | RS, % | 0.15 | 0.16 | 0.17 | 0.15 | — |
| | pH | 7.4 | 7.4 | 7.5 | 7.3 | 7.3 |
| | Osmolality, mOsmol/kg | 276 | 279 | 288 | 283 | 295 |

TABLE 2A-continued

Stability of Example Cevimeline Formulations

| Formulation | Parameter | Time 0 | Storage condition 25° C./60% RH Time, months 3 | 6 | 10 | 27 |
|---|---|---|---|---|---|---|
| | Physical appearance | Colourless, clear solution (CC) | CC | CC | CC | CC |
| Cevi-3 | Assay, % | 102.1 | 100.7 | 101.6 | 100.6 | 100.8 |
| | RS, % | 0.14 | 0.16 | 0.16 | 0.16 | −0.06 |
| | pH | 7.3 | 7.3 | 7.1 | 7.1 | 7.2 |
| | Osmolality, mOsmol/kg | 284 | 296 | 302 | 303 | 306 |
| | Physical appearance | Colourless, clear solution (CC) | CC | CC | CC | CC |
| Cevi-4 | Assay, % | 102.6 | 100.8 | 99.0 | 100.5 | 101.2 |
| | RS, % | 0.15 | 0.17 | 0.15 | 0.14 | — |
| | pH | 7.3 | 7.2 | 7.2 | 7.0 | 7.3 |
| | Osmolality, mOsmol/kg | 296 | 300 | 297 | 303 | 308 |
| | Physical appearance | Colourless, clear solution (CC) | CC | CC | CC | CC |
| Cevi-5 | Assay, % | 103.3 | 102.4 | 99.3 | 102.2 | 102.6 |
| | RS, % | 0.15 | 0.18 | 0.17 | 0.24 | 0.4 |
| | pH | 7.3 | 7.1 | 7.1 | 7.1 | 7.3 |
| | Osmolality, mOsmol/kg | 324 | 325 | 334 | 332 | 336 |
| | Physical appearance | Colourless, clear solution (CC) | CC | CC | CC | CC |
| Cevi-6 | Assay, % | 102.3 | 102.3 | 95.1 | 102.3 | 102.8 |
| | RS, % | 0.15 | 0.18 | 0.16 | 0.16 | — |
| | pH | 7.3 | 7.2 | 7.2 | 7.2 | 7.3 |
| | Osmolality, mOsmol/kg | 314 | 329 | 329 | 327 | 338 |
| | Physical appearance | Colourless, clear solution (CC) | CC | CC | CC | CC |
| Cevi-7 | Assay, % | 97.9 | 97.6 | 97.1 | 97.1 | 97.1 |
| | RS, % | 0.17 | 0.18 | 0.17 | 0.18 | — |
| | pH | 7.5 | 7.4 | 7.2 | 7.3 | 7.2 |
| | Osmolality, mOsmol/kg | 270 | 274 | 276 | 281 | 287 |
| | Physical appearance | Colourless, clear solution (CC) | CC | CC | CC | CC |
| Cevi-8 | Assay, % | 100.2 | 102.5 | 92.0 | 100.8 | 96.4 |
| | RS, % | 0.16 | 0.18 | 0.16 | 0.18 | — |
| | pH | 7.4 | 7.3 | 7.4 | 7.4 | 7.3 |
| | Osmolality, mOsmol/kg | 293 | 294 | 301 | 293 | 306 |
| | Physical appearance | Colourless, clear solution (CC) | CC | CC | CC | CC |

TABLE 2B

| Stability of Example Cevimeline Formulations | | | | | | |
|---|---|---|---|---|---|---|
| | | Time | Storage condition 40° C./75% RH Time, months | | | |
| Formulation | Parameter | 0 | 1 | 2 | 3 | 6 |
| Cevi-1 | Assay, % | 100.8 | 99.1 | 98.8 | 100.2 | 98.9 |
| | RS, % | 0.15 | 0.14 | 0.14 | 0.16 | 0.27 |
| | pH | 7.3 | 7.3 | 7.5 | 7.4 | 7.3 |
| | Osmolality, mOsmol/kg | 287 | 289 | 292 | 284 | 289 |
| | Physical appearance | Colourless, clear solution (CC) | CC | CC | CC | CC |
| Cevi-2 | Assay, % | 100.6 | 99.1 | 100.0 | 98.5 | 97.6 |
| | RS, % | 0.15 | 0.14 | 0.14 | 0.86 | 0.14 |
| | pH | 7.4 | 7.4 | 7.5 | 7.5 | 7.4 |
| | Osmolality, mOsmol/kg | 276 | 290 | 287 | 282 | 284 |
| | Physical appearance | Colourless, clear solution (CC) | CC | CC | CC | CC |
| Cevi-3 | Assay, % | 102.1 | 100.4 | 100.9 | 101.5 | 98.5 |
| | RS, % | 0.14 | 0.14 | 0.14 | 0.15 | 0.27 |
| | pH | 7.3 | 7.3 | 7.3 | 7.3 | 7.3 |
| | Osmolality, mOsmol/kg | 284 | 284 | 304 | 298 | 298 |
| | Physical appearance | Colourless, clear solution (CC) | CC | CC | CC | CC |
| Cevi-4 | Assay, % | 102.6 | 100.5 | 100.2 | 101.6 | 98.6 |
| | RS, % | 0.15 | 0.13 | 0.13 | 0.16 | 0.16 |
| | pH | 7.3 | 7.3 | 7.4 | 7.3 | 7.3 |
| | Osmolality, mOsmol/kg | 296 | 306 | 299 | 298 | 299 |
| | Physical appearance | Colourless, clear solution (CC) | CC | CC | CC | CC |
| Cevi-5 | Assay, % | 103.3 | 103.1 | 103.5 | 102.6 | 100.3 |
| | RS, % | 0.15 | 0.14 | 0.14 | 0.16 | 0.49 |
| | pH | 7.3 | 7.3 | 7.4 | 7.3 | 7.3 |
| | Osmolality, mOsmol/kg | 324 | 337 | 326 | 326 | 329 |
| | Physical appearance | Colourless, clear solution (CC) | CC | CC | CC | CC |
| Cevi-6 | Assay, % | 102.3 | 103.6 | 103.1 | 103.1 | 100.4 |
| | RS, % | 0.15 | 0.14 | 0.15 | 0.16 | 0.37 |
| | pH | 7.3 | 7.2 | 7.3 | 7.2 | 7.1 |
| | Osmolality, mOsmol/kg | 314 | 336 | 328 | 332 | 330 |
| | Physical appearance | Colourless, clear solution (CC) | CC | CC | CC | CC |
| Cevi-7 | Assay, % | 97.9 | 98.0 | 97.8 | 98.1 | 96.1 |
| | RS, % | 0.17 | 0.15 | 0.16 | 0.16 | 0.16 |
| | pH | 7.5 | 7.4 | 7.5 | 7.4 | 7.4 |
| | Osmolality, mOsmol/kg | 270 | 283 | 277 | 273 | 279 |
| | Physical appearance | Colourless, clear solution (CC) | CC | CC | CC | CC |

TABLE 2B-continued

Stability of Example Cevimeline Formulations

| Formulation | Parameter | Time 0 | Storage condition 40° C./75% RH Time, months 1 | 2 | 3 | 6 |
|---|---|---|---|---|---|---|
| Cevi-8 | Assay, % | 100.2 | 101.0 | 101.4 | 99.2 | 99.2 |
| | RS, % | 0.16 | 0.16 | 0.16 | 0.17 | 0.17 |
| | pH | 7.4 | 7.4 | 7.5 | 7.5 | 7.4 |
| | Osmolality, mOsmol/kg | 293 | 298 | 295 | 294 | 295 |
| | Physical appearance | Colourless, clear solution (CC) | CC | CC | CC | CC |

TABLE 2C

Stability of Example Cevimeline Formulations

| Formulation | Parameter | Time 0 | Storage condition 60° C. Time, weeks 3 | 6 |
|---|---|---|---|---|
| Cevi-1 | Assay, % | 100.8 | 103.0 | 98.7 |
| | RS, % | 0.15 | 0.14 | 0.13 |
| | pH | 7.3 | 7.4 | 7.4 |
| | Osmolality, mOsmol/kg | 287 | 292 | 300 |
| | Physical appearance | Colourless, clear solution (CC) | CC | CC |
| Cevi-2 | Assay, % | 100.6 | 99.3 | 98.7 |
| | RS, % | 0.15 | 0.13 | 0.13 |
| | pH | 7.4 | 7.5 | 7.4 |
| | Osmolality, mOsmol/kg | 276 | 292 | 294 |
| | Physical appearance | Colourless, clear solution (CC) | CC | CC |
| Cevi-3 | Assay, % | 102.1 | 100.5 | 99.3 |
| | RS, % | 0.14 | 0.13 | 0.13 |
| | pH | 7.3 | 7.4 | 7.2 |
| | Osmolality, mOsmol/kg | 284 | 301 | 301 |
| | Physical appearance | Colourless, clear solution (CC) | CC | CC |
| Cevi-4 | Assay, % | 102.6 | 100.5 | 98.9 |
| | RS, % | 0.15 | 0.13 | 0.13 |
| | pH | 7.3 | 7.4 | 7.2 |
| | Osmolality, mOsmol/kg | 296 | 301 | 301 |
| | Physical appearance | Colourless, clear solution (CC) | CC | CC |
| Cevi-5 | Assay, % | 103.3 | 102.0 | 99,5 |
| | RS, % | 0.15 | 0.20 | 0.30 |
| | pH | 7.3 | 7.3 | 7.1 |
| | Osmolality, mOsmol/kg | 324 | 330 | 315 |
| | Physical appearance | Colourless, clear solution (CC) | CC | CC |
| Cevi-6 | Assay, % | 102.3 | 102.5 | 99.9 |
| | RS, % | 0.15 | 0.18 | 0.25 |
| | pH | 7.3 | 7.4 | 7.1 |
| | Osmolality, mOsmol/kg | 314 | 325 | 333 |
| | Physical appearance | Colourless, clear solution (CC) | CC | CC |
| Cevi-7 | Assay, % | 97.9 | 96.4 | 96.3 |
| | RS, % | 0.17 | 0.15 | 0.16 |
| | pH | 7.5 | 7.5 | 7.3 |
| | Osmolality, mOsmol/kg | 270 | 288 | 272 |
| | Physical appearance | Colourless, clear solution (CC) | CC | CC |
| Cevi-8 | Assay, % | 100.2 | 101.6 | 99.8 |
| | RS, % | 0.16 | 0.15 | 0.16 |
| | pH | 7.4 | 7.4 | 7.3 |
| | Osmolality, mOsmol/kg | 293 | 299 | 299 |
| | Physical appearance | Colourless, clear solution (CC) | CC | CC |

Example 6

Formulations as described herein are evaluated for irritancy by the Draize eye test in rabbits, which is well known in the literature. Repeated instillations with the formulations are well tolerated by the rabbit ocular surface without any obvious signs of toxicity.

Example 7

A formulation comprising MRA and another active ingredient is prepared according to any one of Examples 1-4 but further including said another active ingredient in an amount (concentration) desired or as described herein.

Example 8

A PUFA and MRA mixture or ion-pair containing composition is prepared as follows. Cevimeline PUFA formulations are generally prepared as follows. Cevimeline HCl salt is added and dissolved in an aqueous solution containing PUFA to prepare a concentrated cevimeline PUFA mixture. One or more surfactants may be added along with PUFA in this step. The concentrated mixture is homogenized under high shear homogenization to form a translucent to milky mixture. A stock solution containing citric acid and sodium phosphate as buffering agents, sodium chloride as a tonicity agent, benzalkonium chloride as a preservative is then mixed with the ion pair mixture to achieve cevimeline concentration of 0.1% to 10%. Edetate disodium (EDTA) may be added at a concentration of 0.01 to 0.2%. At least one suitable antioxidant may be added. At least one surfactant may be added. At least one viscosity agent may be added in this stock solution. Hydrochloric acid and/or sodium hydroxide may be added to adjust the pH to ~7.4 if necessary. The composition is sterile filtered through a 0.22 micron filter.

Accordingly, the aqueous ophthalmic composition of the invention is stable at a neutral pH range.

All values disclosed herein may have standard technical measure error (standard deviation) of ±10%. The term "about" is intended to mean±10%, ±5%, ±2.5% or ±1% relative to a specified value, i.e. "about" 20% means 20±2%, 20±1%, 20±0.5% or 20±0.25%.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

We claim:

1. A stable aqueous liquid topical ophthalmic composition comprising about 0.1% to 10% of cevimeline at a neutral pH range of pH 6-7.5, and one or more pharmaceutically acceptable excipients.

2. The composition of claim 1, wherein cevimeline is present as the free base form, salt form, or a combination of free base and salt form, and further comprising a second active ingredient, wherein the second active ingredient comprises a steroid, an immunomodulator, an immunosuppressant, a hormone, an androgen, a secretagogue, a lymphocyte function associated antigen-1 (LFA-1) antagonist, an active ingredient which is effective for treating Meibomian gland dysfunction, or a combination thereof.

3. The composition of claim 1, wherein the cevimeline is present at a concentration of about 0.5% to about 5% w/v.

4. The composition of claim 3, wherein the cevimeline is present at a concentration of about 0.2% to about 2% w/v.

5. The composition of claim 1, further comprising at least one polyunsaturated fatty acid (PUFA).

6. The composition of claim 5, wherein the PUFA is present at a concentration of about 0.1% to about 10% w/v, about 0.5% to about 5% w/v, or about 0.2% to about 2% w/v.

7. The composition of claim 5, wherein said PUFA comprises about 12 to about 26 carbon atoms per molecule.

8. The composition of claim 5, wherein said PUFA is an omega-3 fatty acid, an omega-6 fatty acid, or a mixture thereof.

9. The composition of claim 5, wherein said PUFA is eicosapentaenoic acid (EPA), docosahexaenoic acid (DHA), alpha-linolenic acid (ALA), gamma-linolenic acid (GLA), or a mixture thereof.

10. The composition of claim 1, further comprising a buffering agent and a tonicity modifier.

11. The composition of claim 10, further comprising a preservative, a chelating agent, a viscosity-modifying agent, a surfactant, a solubilizer, an antioxidant, or a combination thereof.

12. The composition of claim 2, wherein a) said steroid is present at a concentration in the range of about 0.1% to about 1% w/v; b) said immunomodulator is present at a concentration in the range of about 0.05% to about 0.1% w/v; c) said hormone is present at a concentration in the range of about 0.01% to about 0.5% w/v; or d) said secretagogue is present at a concentration in the range of about 1% to about 5% w/v; or e) said lymphocyte function associated antigen-1 (LFA-1) antagonist in the range of about 1% to about 5% w/v.

13. The composition of claim 2, wherein a) said steroid is loteprednol etabonate, prednisolone acetate, fluticasone, or a combination thereof; b) said immunomodulator is cyclosporine, tacrolimus, sirolimus, or a combination thereof; c) said hormone is testosterone, estrogen, or a combination thereof; d) said secretagogue is rebamipide, diquafosol, or a combination thereof; or e) said lymphocyte function associated antigen-1 (LFA-1) antagonist is lifitegrast.

14. The composition of claim 1, wherein said composition excludes an ointment composition, cream composition, plaster composition, and paste composition.

15. The composition of claim 1, wherein said composition excludes insulin, IGF (insulin-like growth factor), somatomedin C, and cycloplegic agent.

16. The composition of claim 1, wherein the neutral pH range is pH 6-7.0.

17. A method of treating dry eye disease comprising topically administering to the eye of a subject in need thereof, a composition according to claim 1.

* * * * *